(12) United States Patent
Matsuzawa et al.

(10) Patent No.: US 10,039,278 B2
(45) Date of Patent: Aug. 7, 2018

(54) DEVICE FOR VITRIFICATION PRESERVATION OF CELLS OR TISSUES

(71) Applicant: MITSUBISHI PAPER MILLS LIMITED, Tokyo (JP)

(72) Inventors: Atsushi Matsuzawa, Tokyo (JP); Katsumitsu Susaki, Tokyo (JP)

(73) Assignee: MITSUBISHI PAPER MILLS LIMITED, Tokyo (JP)

( * ) Notice: Subject to any disclaimer, the term of this patent is extended or adjusted under 35 U.S.C. 154(b) by 13 days.

(21) Appl. No.: 15/322,849

(22) PCT Filed: Jun. 1, 2015

(86) PCT No.: PCT/JP2015/065754
§ 371 (c)(1),
(2) Date: Dec. 29, 2016

(87) PCT Pub. No.: WO2016/002410
PCT Pub. Date: Jan. 7, 2016

(65) Prior Publication Data
US 2017/0135335 A1    May 18, 2017

(30) Foreign Application Priority Data
Jun. 30, 2014 (JP) ................. 2014-134084

(51) Int. Cl.
*A01N 1/02* (2006.01)
(52) U.S. Cl.
CPC .......... *A01N 1/0252* (2013.01); *A01N 1/0221* (2013.01)

(58) Field of Classification Search
CPC .................. A01N 1/0252; A01N 1/0221
See application file for complete search history.

(56) References Cited

U.S. PATENT DOCUMENTS

| | | |
|---|---|---|
| 2004/0065093 A1 | 4/2004 | Fuhr et al. |
| 2009/0311297 A1 | 12/2009 | Hontsu et al. |
| 2012/0251752 A1 | 10/2012 | Hayashi et al. |
| 2016/0057991 A1 | 3/2016 | Matsuzawa et al. |

FOREIGN PATENT DOCUMENTS

| | | |
|---|---|---|
| CN | 101111603 A | 1/2008 |
| CN | 101400784 A | 4/2009 |
| CN | 101522856 A | 9/2009 |

(Continued)

OTHER PUBLICATIONS

Momozawa, K. et al., "Vitrification of bovine blastocysts on a membrane filter absorbing extracellular vitrification solution" J. Mamm. Ova Res., Apr. 1, 2006, vol. 23, No. 1, pp. 63-66 (5 pages).

(Continued)

*Primary Examiner* — Gautam Prakash
(74) *Attorney, Agent, or Firm* — Osha Liang LLP (57) ABSTRACT

The present invention aims to provide a device for vitrification cryopreservation enabling easy and reliable vitrification cryopreservation of a cell or tissue. The device for vitrification cryopreservation of a cell or tissue of the present invention includes a support and a vitrification solution absorber including at least an adhesive layer and a vitrification solution absorbing layer in the given order on the support. The device includes a portion with no adhesive layer disposed between the support and a portion of the vitrification solution absorbing layer configured to hold a cell or tissue.

2 Claims, 2 Drawing Sheets

(56) References Cited

FOREIGN PATENT DOCUMENTS

| | | | |
|---|---|---|---|
| CN | 102753677 A | 10/2012 |
| CN | 103179852 A | 6/2013 |
| CN | 203340879 U | 12/2013 |
| CN | 203369308 U | 1/2014 |
| JP | H02-117381 A | 5/1990 |
| JP | H10-248860 A | 9/1998 |
| JP | 3044323 B1 | 5/2000 |
| JP | 2002-315573 A | 10/2002 |
| JP | 2005-040073 A | 2/2005 |
| JP | 2006-271395 A | 10/2006 |
| JP | 2008-005846 A | 1/2008 |
| JP | 2008-222640 A | 9/2008 |
| JP | 2013-111017 A | 6/2013 |
| WO | 2006/058286 A2 | 6/2006 |
| WO | 2008/018966 A2 | 2/2008 |
| WO | 2011/070973 A1 | 6/2011 |
| WO | 2011/146998 A1 | 12/2011 |
| WO | 2014/185457 A1 | 11/2014 |

OTHER PUBLICATIONS

Steponkus P. L. et al., "Cryopreservation of *Drosophila melanogaster* embryos" Letters to Nature, 345:170-172 (1990) (3 pages).
Japanese Society of Animal Science Annual Meeting Abstracts, vol. 112th, p. 88, Mar. 28, 2010 (5 pages).
International Search Report issued in PCT/JP2015/065754, dated Aug. 4, 2015 (2 pages).
Written Opinion of the International Searching Authority issued in PCT/JP2015/065754, dated Aug. 4, 2015 (4 pages).
Lee, Kun-Hsiung et al., "An efficient and mass reproducible method for vitrifying mouse embryos on a paper in cryotubes," Cryobiology, Academic Press Inc., US, vol. 66, No. 3, p. 311-317, dated Mar. 28, 2013 (7 pages).
Kim, Y.M. et al., "Successful vitrification of bovine blastocysts on paper container," Theriogenology, vol. 78, No. 5, p. 1085-1093, dated Sep. 1, 2012 (9 pages).
Office Action issued in Korean Application No. 10-2017-7000907, dated Jun. 21, 2018 (6 pages).

DEVICE FOR VITRIFICATION PRESERVATION OF CELLS OR TISSUES

TECHNICAL FIELD

The present invention relates to devices for vitrification cryopreservation to be used for cryopreserving biological cells or tissues, for example.

BACKGROUND ART

Excellent preservation techniques for biological cells or tissues are desired in various industrial fields. For example, in the bovine embryo transfer technology, embryos are transferred in consideration of the estrus cycle of a recipient cow. In order to synchronize the transfer of embryos with the estrus cycle, embryos are cryopreserved in advance and are thawed and transferred in time with the estrus cycle. In the human fertility treatment, eggs or ovaries are harvested from a woman's body and cryopreserved until an appropriate timing for transplantation, and the cryopreserved eggs or ovaries are thawed before the use in transplantation.

In general, cells or tissues harvested from living bodies gradually become inactive even in a culture medium, and hence long-term culture of cells or tissues in vitro is undesirable. For this reason, techniques for long-term preservation of cells or tissues without the loss of biological activity are essential. Excellent preservation techniques enable more accurate analysis of cells or tissues harvested. Such excellent preservation techniques also enable transplantation of cells or tissues with their biological activity kept at a higher level, thus likely resulting in an improvement in the engraftment rate. The techniques also enable in-advance production and preservation of artificial tissues for transplantation, such as skins cultured in vitro and what they call cell sheets formed in vitro, and storage thereof until needed. Therefore, such excellent preservation techniques are expected to bring great advantages not only in the industrial fields but also in the medical science fields.

One of known methods for preserving cells or tissues is slow freezing, for example. In this method, cells or tissues are immersed in a preservation solution prepared by adding a cryoprotectant to a physiological solution such as phosphate buffered saline. Examples of the cryoprotectant include compounds such as glycerol and ethylene glycol. The cells or tissues immersed in the preservation solution are cooled down to −30° C. to −35° C. at a relatively slow cooling rate (for example, 0.3° C. to 0.5° C./min), and thereby the solution inside and outside the cells or tissues are sufficiently cooled and become viscous. Further cooling down the cells or tissues in such a state in the preservation solution to the temperature of liquid nitrogen (−196° C.) allows a slight amount of the solution both inside and outside (surrounding) the cells or tissues to become a solid while the amorphous state thereof is maintained, that is, to vitrify. The vitrification (i.e., solidification) of the solution inside and outside the cells or tissues substantially immobilizes the molecules. Thus, the vitrified cells or tissues can be semipermanently preserved in liquid nitrogen.

However, since the slow freezing requires relatively slow-rate cooling, the procedure of cryopreservation takes a long time. Further, this technique disadvantageously needs the use of a temperature-controlling device or jig. In addition, the slow freezing cannot avoid formation of ice crystals in the preservation solution outside the cells or tissues, which may cause physical damage to the cells or tissues.

One proposed solution to the problems of the slow freezing is vitrification cryopreservation. The vitrification cryopreservation is a technique using a principle that addition of a large amount of a cryoprotectant, such as glycerol, ethylene glycol, or dimethyl sulfoxide (DMSO), to water decreases the freezing point of water, thereby restraining formation of ice crystals at sub-zero temperatures. When quickly cooled in liquid nitrogen, such an aqueous solution can solidify without formation of ice crystals. This solidification is called vitrification freezing. The aqueous solution containing a large amount of a cryoprotectant is called a vitrification solution.

The specific procedure of the vitrification cryopreservation is to immerse cells or tissues in a vitrification solution and to cool them at the temperature of liquid nitrogen (−196° C.). Since the vitrification is such a simple and quick process, it advantageously does not require a long-term procedure of cryopreservation or the use of any temperature-controlling device or jig.

The vitrification cryopreservation does not cause formation of ice crystals either inside or outside the cells, and thus can avoid physical damage (freezing damage) to the cells at the time of freezing and thawing. However, a high-concentration cryoprotectant contained in the vitrification solution is chemically toxic. Thus, the volume of the vitrification solution around cells or tissues used in cryopreservation of the cells or tissues is preferably as small as possible. Further, the duration of exposure of the cells to the vitrification solution, that is, the time until freezing, is preferably short. In addition, the vitrification solution needs to be diluted immediately after thawing.

Various examples of the vitrification-based cryopreservation of cells or tissues have been reported using various methods and various cells or tissues. For example, Patent Literature 1 discloses that application of the vitrification cryopreservation to reproductive or somatic cells of animal or human origin is very useful in terms of the cell viability after cryopreservation and thawing.

The vitrification cryopreservation is a technique which has been developed mainly using human reproductive cells. More recently, its application to iPS or ES cells has also been widely examined. Non-Patent Literature 1 discloses the effectiveness of the vitrification cryopreservation in preservation of *Drosophila* embryos. Patent Literature 2 discloses the effectiveness of the vitrification cryopreservation in preservation of plant culture cells and tissues. As mentioned here, the vitrification is known to be useful for preservation of a wide range and different kinds of cells and tissues.

With regard to devices and procedures for more efficient vitrification cryopreservation, Patent Literature 3, for example, reports an attempt to improve the recovery rate of cryopreserved eggs or embryos by vitrifying them in a straw filled with a vitrification solution, and then bringing them into contact with a diluent immediately in thawing.

Patent Literature 4 proposes a cryopreservation method with excellent viability including depositing eggs or embryos together with a vitrification solution on a removing material for vitrification preservation and removing an excess vitrification solution surrounding the eggs or embryos by downward suction. Examples of the removing material for vitrification cryopreservation disclosed include wire mesh and perforated films made of natural substance, such as paper, or synthetic resin.

Patent Literature 5 proposes a cryopreservation method with excellent viability including absorbing an excess vitrification solution surrounding eggs or embryos with an absorber such as filter paper.

Patent Literature 6 and Patent Literature 7 propose a cryopreservation method, what is called the Cryotop method, used in the field of human fertility treatment. This method uses a tool for cryopreservation of eggs including a flexible, clear and colorless film strip as an egg-holding strip, and includes depositing eggs or embryos together with a very small amount of a vitrification solution on the film under a microscope.

Patent Literature 8 proposes a method of producing frozen cell sheets by the vitrification including placing a cell sheet together with a transfer-support film (Cell Shifter, a sheet mainly made of cellulose, available from CellSeed Inc., or a PVDF film) on a pedestal made of, for example, a wire mesh, absorbing or discharging an excess vitrification solution, and then cryopreserving the cell sheet.

CITATION LIST

Patent Literature

Patent Literature 1: JP 3044323 B
Patent Literature 2: JP 2008-5846 A
Patent Literature 3: JP H10-248860 A
Patent Literature 4: WO 2011/070973
Patent Literature 5: JP 2005-40073 A
Patent Literature 6: JP 2002-315573 A
Patent Literature 7: JP 2006-271395 A
Patent Literature 8: JP 2013-111017 A Non-Patent Literature Non-Patent Literature 1: Steponkus et al., Nature 345:170-172 (1990)

SUMMARY OF INVENTION

Technical Problem

The method proposed in Patent Literature 3 involves filling up a straw with a vitrification solution, and thus freezing of the vitrification solution unfortunately takes a long time. Further, the size of cells or tissues to be cryopreserved is limited by the inner diameter of the straw, making it difficult to preserve a large number of cells or a sheet-like tissue such as a cell sheet.

The method proposed in Patent Literature 4 is for cryopreservation of eggs or embryos with excellent viability by removing an excess vitrification solution surrounding these reproductive cells. However, the removal of an excess vitrification solution in the method disclosed in this literature requires downward suction, making the procedure complicated. Thus, this method is unsuitable for quick completion of the vitrification cryopreservation procedure. Another problem is that an excess vitrification solution may remain if the downward suction is insufficient.

Patent Literature 5 proposes a method for cryopreservation of eggs or embryos with excellent viability by absorbing an excess vitrification solution surrounding these reproductive cells with an absorber such as filter paper. However, in vitrification of cell populations including cells stacked on one another or tissues, a relatively large amount of a vitrification solution is used. This causes the absorber to have insufficient strength, poor self-supportability, and significantly reduced handleability.

Patent Literature 6 and Patent Literature 7 each propose a method for cryopreservation of eggs or embryos together with a small amount of a vitrification solution by limiting the width of a film on which eggs or embryos are to be deposited. In this method, a worker manually deposits eggs or embryos together with a very small amount of a vitrification solution on a film, but this operation is very difficult. In order to cryopreserve eggs or embryos together with a smaller amount of a vitrification solution, the Cryotop method based on this method sometimes includes a complicated procedure, i.e., depositing eggs or embryos together with a vitrification solution on a film and then suction-removing an excess vitrification solution from the top of the film. Further, this method is unsuitable for cryopreservation of sheet-like tissues having a large area, such as cell sheets.

Patent Literature 8 discloses a method including depositing a cell sheet together with a transfer-support film (Cell Shifter available from CellSeed Inc. or a polyvinylidene fluoride (PVDF) film) on a pedestal such as a glass plate, metal plate, wire mesh, or nonwoven fabric, sucking or discharging an excess vitrification solution, and then cryopreserving the cell sheet. However, if a large amount of the vitrification solution is dropped with cells or tissues, the vitrification solution is sucked at an insufficient rate, and thus an excess vitrification solution remains. Further, Cell Shifter or a PVDF film is usually a film-like structure and has poor self-supportability. Thus, such films have difficulty in facilitating freezing and thawing procedures.

One main object of the present invention is to provide a device for vitrification cryopreservation which enables easy and reliable cryopreservation of a cell or tissue. Specifically, a first object of the present invention is to provide a device for vitrification cryopreservation having excellent performance of absorbing an excess vitrification solution after a cell or tissue is immersed in the vitrification solution and then deposited on the device together with the vitrification solution for vitrification cryopreservation. A second object of the present invention is to provide a device for vitrification cryopreservation having excellent visibility in addition to the above excellent performance of absorbing the vitrification solution. Such visibility enables observation of a cell or tissue deposited together with the vitrification solution on the device for vitrification cryopreservation under a transmission microscope.

Solution to Problem

The inventors have performed studies to solve the above problems, and found that a device for vitrification cryopreservation of a cell or tissue (hereinafter, the "device for vitrification cryopreservation of a cell or tissue" is also referred to simply as a "device for vitrification cryopreservation") having the following configuration can solve the problems.

(1) A device for vitrification cryopreservation of a cell or tissue, including: a support; and a vitrification solution absorber including at least an adhesive layer and a vitrification solution absorbing layer in the given order on the support, the device including a portion with no adhesive layer disposed between the support and a portion of the vitrification solution absorbing layer configured to hold a cell or tissue.

(2) The device for vitrification cryopreservation of a cell or tissue according to the above embodiment (1), wherein the support is a light-transmitting support, and the vitrification solution absorbing layer is at least one selected from paper or nonwoven fabric having a density of 0.12 to 0.3 g/cm³ and a grammage of 10 to 100 g/m², porous resin sheets, and porous metal oxide sheets.

Advantageous Effects of Invention

According to the embodiment (1), after a cell or tissue is immersed in a vitrification solution and is then deposited on the vitrification solution absorber, the vitrification solution absorber absorbs an excess vitrification solution surrounding the cell or tissue. Thus, the embodiment provides a device for vitrification cryopreservation of a cell or tissue which enables easy and simple cryopreservation of a cell or tissue without the need of additional procedures for removing the excess vitrification solution (for example, downward suction removal through the vitrification solution absorber or direct suction removal from the periphery of the cell or tissue using a micropipette). In addition to this effect, the embodiment (2) can provide a device for vitrification cryopreservation providing excellent visibility of a cell or tissue. Therefore, use of the device for vitrification cryopreservation of the present invention enables efficient vitrification freezing and thawing of a cell or tissue.

DESCRIPTION OF EMBODIMENTS

The device for vitrification cryopreservation of the present invention is used for cryopreservation of a cell or tissue of a living organism. The cell herein encompasses not only a single cell but also a cell population composed of multiple cells. The cell population composed of multiple cells may be a cell population composed of a single kind of cells or may be a cell population composed of multiple kinds of cells. The tissue may be composed of a single kind of cells or may be composed of multiple kinds of cells, or may contain a non-cellular substance like an extracellular matrix in addition to cells.

The device for vitrification cryopreservation of the present invention is to be preferably used in a process including: depositing a cell or tissue with a vitrification solution on a vitrification solution absorber, and then immersing and freezing the cell- or tissue-holding device in a coolant such as liquid nitrogen. The vitrification solution absorber facilitates holding of the cell or tissue with the vitrification solution and reliably holds the cell or tissue even during freezing or thawing, facilitating the immersion of the cell or tissue in liquid nitrogen. Further, the device for vitrification cryopreservation of the present invention can provide excellent visibility of a cell or tissue, enabling easy observation of the cell or tissue deposited on the vitrification solution absorber. Thus, use of the device for vitrification cryopreservation of the present invention enables easy and reliable procedures for cryopreservation of a cell or tissue. The device for vitrification cryopreservation of the present invention can be said in different words, such as a device for cryopreservation of a cell or tissue, a device for vitrification preservation of a cell or tissue, a tool for cryopreservation of a cell or tissue, and a tool for vitrification preservation of a cell or tissue.

The device for vitrification cryopreservation of the present invention includes a vitrification solution absorber, and the vitrification solution absorber absorbs an excess vitrification solution surrounding the cell or tissue. Thus, even if a cell or tissue immersed in the vitrification solution is deposited on the vitrification solution absorber with a large amount of the vitrification solution, the viability of the cell or tissue is expected to be stable. Further, the cell or tissue after such a procedure is covered with a very small amount of the vitrification solution, and thus can be quickly frozen during the freezing procedure. In addition, the vitrification solution can be diluted immediately after the cryopreserved cell or tissue is thawed.

The following will describe the configuration of the device for vitrification cryopreservation of the present invention.

The device for vitrification cryopreservation of the present invention is a device for vitrification cryopreservation of a cell or tissue including a support and a vitrification solution absorber disposed on the support, the vitrification solution absorber including at least an adhesive layer and a vitrification solution absorbing layer in the given order, and the device including a portion with no adhesive layer disposed between the support and a portion of the vitrification solution absorbing layer configured to hold a cell or tissue. The portion of the vitrification solution absorbing layer configured to hold a cell or tissue herein means a portion of the vitrification solution absorbing layer where a cell or tissue is to be in contact with the vitrification solution absorbing layer after the cell or tissue with a vitrification solution is deposited dropwise on the vitrification solution absorbing layer. The device for vitrification cryopreservation of the present invention most preferably has no adhesive layer between the vitrification solution absorbing layer and the support in the portion of the vitrification solution absorbing layer configured to hold a cell or tissue. Still, if the proportion of the area of the adhesive layer to the area of the portion configured to hold a cell or tissue falls within a range of smaller than 20%, more preferably smaller than 10%, the device may have an adhesive layer even in the portion configured to hold a cell or tissue. The device for vitrification cryopreservation of the present invention may consist only of the vitrification solution absorber, or may include other components which do not impair the effects of the invention, such as a gripper to be mentioned later, in addition to the vitrification solution absorber.

Examples of the vitrification solution absorbing layer of the vitrification solution absorber in the present invention include various sheets such as fibrous sheets, porous resin sheets, porous metal sheets, and porous metal oxide sheets. The term "porous" herein means that the sheet is a structure having pores (small cavities) on the surface thereof. The sheet is more preferably a structure having open pores on the surface of and inside the sheet. The vitrification solution absorbing layer (any of the above various sheets) preferably has a thickness of 10 μm to 5 mm, more preferably 20 μm to 2.5 mm.

In order to quickly and easily immerse a cell or tissue in a very low temperature cooling solvent (e.g., liquid nitrogen at −196° C.) for cryopreservation, the vitrification solution absorber preferably includes a support. This enables an increase in the self-supportability or strength of the vitrification solution absorber, improving the handleability. Unfortunately, devices for vitrification cryopreservation including a vitrification solution absorbing layer disposed on a support with an adhesive layer interposed therebetween suffer entering of part of the adhesive layer into voids of the vitrification solution absorbing layer, impairing the performance of absorbing the vitrification solution. The present invention solves such a problem by providing a device for vitrification cryopreservation including a portion with no adhesive layer disposed between the support and the portion of the vitrification solution absorbing layer configured to hold a cell or tissue.

In the present invention, the fibrous sheet to be used as the vitrification solution absorbing layer may be paper or nonwoven fabric, for example.

The paper preferably satisfies that the proportion of binding agent components such as a binder in the whole paper is 10 mass % or less, more preferably 5 mass % or less, still more preferably 3 mass % or less. This may lead to excellent vitrification solution absorbency. The proportion of papermaking chemicals contained in the vitrification solution absorbing layer in the whole paper is preferably 1 mass % or less. Chemicals such as fluorescent brighteners, dyes, and cationic sizing agents among papermaking chemicals usually contained in paper may disadvantageously affect cells.

If the fibrous sheet is paper, it preferably has a density of 0.1 to 0.6 g/cm$^3$ and a grammage of 10 to 130 g/m$^2$. In order to provide a device for vitrification cryopreservation having excellent vitrification solution absorbency as well as providing excellent visibility of a cell or tissue, the paper preferably has a density of 0.12 to 0.3 g/cm$^3$ and a grammage of 10 to 100 g/m$^2$.

If the fibrous sheet is nonwoven fabric, examples of the fiber contained in the nonwoven fabric include cellulose fiber, rayon fiber and cupro fiber which are regenerated fibers made from cellulose fiber, acetate fiber which is a semi-synthetic fiber made from cellulose fiber, polyester fiber, nylon fiber, acrylic fiber, polypropylene fiber, polyethylene fiber, polyvinyl chloride fiber, vinylidene fiber, polyurethane fiber, vinylon fiber, glass fiber, and silk fiber. Nonwoven fabric made by mixing fibers among these fibers may also be used. Preferred are cellulose fiber, rayon fiber and cupro fiber which are cellulose regenerated fibers derived from cellulose fiber, as well as acetate fiber which is a semi-synthetic fiber made from cellulose fiber.

If the fibrous sheet is nonwoven fabric, it preferably has a density of 0.1 to 0.4 g/cm$^3$ and a grammage of 10 to 130 g/m$^2$. In order to provide a device for vitrification cryopreservation having excellent vitrification solution absorbency as well as providing excellent visibility of a cell or tissue, the nonwoven fabric preferably has a density of 0.12 to 0.3 g/cm$^3$ and a grammage of 10 to 100 g/m$^2$.

Similar to the case of paper, nonwoven fabric to be used as the vitrification solution absorbing layer also preferably satisfies that the proportion of binding agent components such as a binder in the whole nonwoven fabric is 10 mass % or less, more preferably 5 mass % or less, still more preferably 3 mass % or less. The nonwoven fabric is preferably free from a binding agent.

Different from the case of paper, nonwoven fabric may be produced by various methods. The nonwoven fabric with a reduced proportion of binding agent components is preferably produced by spun-bonding or melt-blowing, and preferably produced by aligning fibers by a wet process or a dry process, and then performing hydroentanglement or needle punching. As mentioned above, the fiber contained in the nonwoven fabric in the present invention is preferably cellulose fiber, rayon fiber or cupro fiber which is a cellulose regenerated fiber derived from cellulose fiber, or acetate fiber which is a semi-synthetic fiber made from cellulose fiber. If the nonwoven fabric is produced using such a fiber, the production method is preferably hydroentanglement or needle punching regardless of whether the fibers are aligned by a wet process or a dry process.

Examples of the porous resin sheet to be used as the vitrification solution absorbing layer in the present invention include resin sheets having a porous structure which is formed of a microfibrous structure prepared by at least uniaxially stretching a resin material and heating the resin material up to a temperature of not lower than the melting point of the resin to sinter the resin material, as disclosed in JP S42-13560 B and JP H08-283447 A; and a resin sheet having a porous structure which is formed by putting solid powder of thermoplastic resin prepared by, for example, emulsion polymerization or pulverization into a mold, heating and sintering the powdery particles to fuse the surfaces of the particles, and then cooling the particles, as disclosed in JP 2009-235417 A. Using a porous resin sheet as the vitrification solution absorbing layer is preferred because it enables production of a device for vitrification cryopreservation having excellent vitrification solution absorbency as well as providing excellent visibility of a cell or tissue.

Examples of the resin constituting the porous resin sheet include polyethylene species such as low-density polyethylene, high-density polyethylene, and ultra high molecular weight polyethylene, polypropylene, polymethyl methacrylate, polystyrene, fluororesins such as polytetrafluoroethylene and polyvinylidene difluoride, ethylene-vinyl acetate copolymers, polyamide, styrene-acrylonitrile copolymers, styrene-butadiene-acrylonitrile terpolymers, polycarbonate, and polyvinyl chloride. In order to provide a device for vitrification cryopreservation particularly providing excellent visibility of a cell or tissue, fluororesins such as polytetrafluoroethylene and polyvinylidene difluoride are preferred. The porous resin sheet may be a membrane filter for filtering which is commercially available for the purposes of physical and chemical experiments and researches.

In the present invention, the porous metal sheet to be used as the vitrification solution absorbing layer may be a porous metal sheet made from a metal such as copper, copper alloy, aluminum, aluminum alloy, gold, gold alloy, silver, silver alloy, tin, zinc, lead, titanium, nickel, or stainless steel. The porous metal oxide sheet may be preferably a porous metal oxide sheet made from a metal oxide such as silica, alumina, zirconium, or quartz glass. The porous metal sheet and the porous metal oxide sheet each may be a porous sheet containing two or more of the metals or the metal oxides. The porous metal oxide sheet is preferred because it enables production of a device for vitrification cryopreservation providing excellent visibility of a cell or tissue.

In the present invention, each of the porous metal sheet and the porous metal oxide sheet to be used as the vitrification solution absorbing layer may be produced by a commonly known method. The porous metal sheet to be used as the vitrification solution absorbing layer may be produced by powder metallurgy or the spacer method. Also, what is called the powder space holder method, which is a combination of resin injection molding and powder metallurgy, may preferably be used. For example, methods disclosed in WO 2006/041118 and JP 4578062 B may be used. Specifically, metal power and a resin serving as a spacer are mixed, and then the mixture is pressure-molded and fired in a high-temperature environment so that the metal powder is sintered and the resin serving as a spacer is evaporated. Thereby, a porous metal sheet is obtained. In the case of the powder space holder method, for example, a resin binder may also be mixed with the metal powder and the resin serving as a spacer. Alternatively, other methods of producing metal porous bodies, such as melt foaming and gas expansion, may be used in which metal powder is heated at high temperature and gas is injected to form voids. Methods of producing metal porous bodies using a foaming agent, such as slurry foaming, may also be used. The porous metal oxide sheet to be used as the vitrification solution absorbing layer may be produced by, for example, methods disclosed in JP 2009-29692 A and JP 2002-160930 A.

In order to improve the performance of absorbing the vitrification solution, the surface of the porous body selected from the above porous resin sheets, porous metal sheets, and porous metal oxide sheets may be hydrophilized. The hydrophilization may be achieved by, for example, graft modification, coating with a hydrophilic polymeric compound, or other common surface modification using any of various energies such as corona discharge, plasma treatment, and excimer laser.

If the vitrification solution absorbing layer in the present invention is a porous body selected from the above porous resin sheets, porous metal sheets, porous metal oxide sheets, and the like, the porous body preferably has a micropore size of 0.02 to 130 μm, more preferably 0.05 to 60 μm. If the micropore size is smaller than 0.02 μm, the performance of absorbing the vitrification solution may be insufficient when the vitrification solution is deposited dropwise. Further, the porous sheet may be difficult to produce. If the micropore size is greater than 130 μm, a cell or tissue may be trapped in the micropores, so that the cell is less likely to be released from the vitrification solution absorber during the thawing procedure. Further, the performance of absorbing the vitrification solution may be insufficient. The micropore size of the porous body, in the case of a porous resin sheet, corresponds to the diameter of the greatest micropore measured by the bubble point test. In the case of a porous metal sheet or a porous metal oxide sheet, the micropore size corresponds to the average micropore diameter determined by image observation of the surface and cross section of the porous body.

The vitrification solution absorbing layer preferably has a porosity of 20 vol % or more, more preferably 30 vol % or more. If the vitrification solution absorbing layer is a porous body such as the aforementioned porous resin sheet, porous metal sheet, or porous metal oxide sheet, the pores inside the porous body preferably form a continuous structure not only in the thickness direction but also in the direction perpendicular to the thickness direction. Such a structure enables effective use of the pores inside the porous body, leading to good performance of absorbing the vitrification solution. The thickness of the vitrification solution absorbing layer and the porosity of the porous body may be appropriately selected in accordance with factors such as the type of a cell or tissue used and the amount of the vitrification solution deposited dropwise with the cell or tissue.

The porosity is defined by the following formula. The void volume V may be determined by mercury intrusion.

$$P=(V/T)\times 100(\%)$$

where
P: porosity (%)
V: void volume (ml/m$^2$)
T: thickness (μm).

The area of the vitrification solution absorber of the device for vitrification cryopreservation of the present invention may be appropriately determined in accordance with factors such as the amount of the vitrification solution deposited dropwise with the cell or tissue, and may be any value. For example, the area thereof is preferably 1 mm$^2$ or larger, more preferably 2 to 400 mm$^2$ per microliter of the vitrification solution deposited dropwise. If the vitrification solution absorber has multiple vitrification solution absorbing layer portions, one continuous vitrification solution absorbing layer portion preferably has the above area.

The area of the portion with no adhesive layer disposed between the vitrification solution absorbing layer and the support in the vitrification solution absorber of the device for vitrification cryopreservation of the present invention may be appropriately determined in accordance with factors such as the size of a cell or tissue and the amount of the vitrification solution deposited dropwise with the cell or tissue, and may be any value. The proportion of the area of the portion with no adhesive layer disposed between the vitrification solution absorbing layer and the support to the area of one continuous vitrification solution absorbing layer is preferably 2 to 70%.

The support of the vitrification solution absorber used in the present invention may be any of commonly known various supports. Examples of such a support include a variety of resin films, metal, glass, and rubber. Two or more supports may be used in combination as long as they provide the effects of the present invention. In view of the visibility of a cell or tissue, a light-transmitting support is preferred, and a light-transmitting support having a total light transmittance of 80% or higher is more preferred. The light-transmitting support also preferably has a haze value of 10% or lower. Examples of such a light-transmitting support include resin films made from polyester resin such as polyethylene terephthalate (PET) and polyethylene naphthalate (PEN), acrylic resin, epoxy resin, silicone resin, polycarbonate resin, diacetate resin, triacetate resin, polyarylate resin, polyvinyl chloride resin, polysulfone resin, polyether sulfone resin, polyimide resin, polyamide resin, polyolefin resin, and cyclic polyolefin resin. In order to achieve excellent thermal conductivity and quick freezing, a metal support is preferably used. Specific examples of the metal support include copper, copper alloy, aluminum, aluminum alloy, gold, gold alloy, silver, silver alloy, iron, and stainless steel. The support preferably has a thickness of 10 μm to 10 mm. In order to increase the adhesion strength with the adhesive layer, the surface of the support may be subjected to adhesion-improving treatment using corona discharge.

The adhesive layer of the vitrification solution absorber in the present invention may contain an adhesive composition such as an instant adhesive composition typified by a moisture-curable adhesive substance, a hot-melt adhesive composition, or a photo-curable adhesive composition. Preferred examples thereof include compositions containing any of water-soluble polymeric compounds such as polyvinyl alcohol, hydroxycellulose, polyvinyl pyrrolidone, and starch paste; and water-insoluble resins such as vinyl acetate resin, acrylic resin, epoxy resin, urethane resin, elastomeric resin, cyanoacrylate resin, fluorine resin, silicone resin, nitrocellulose resin, nitrile rubber resin, styrene-butadiene resin, urea resin, styrene resin, phenolic resin, polyimide resin, polyamide resin, polyester resin, bismaleimide resin, olefinic resin, and EVA resin. The adhesive layer may contain one resin or may contain multiple resins. The adhesive layer preferably has a solid content of 0.01 to 100 g/m$^2$, more preferably 0.1 to 50 g/m$^2$.

The vitrification solution absorber in the present invention has a portion with no adhesive layer disposed between the support and a portion of the vitrification solution absorbing layer configured to hold a cell or tissue. The vitrification solution absorber having such a portion is obtainable by forming a portion not coated with the aforementioned adhesive composition on the support at a portion which is to overlap the portion configured to hold a cell or tissue during formation of the adhesive layer (for example, by masking a portion of the support which is to overlap the portion configured to hold a cell or tissue before application of the adhesive composition), and then stacking any of various sheets such as fibrous sheets, porous resin sheets, porous metal sheets, and porous metal oxide sheets before drying of the adhesive composition.

The vitrification solution absorber of the device for vitrification cryopreservation of the present invention is described hereinabove. As mentioned above, the device for vitrification cryopreservation of the present invention may be any one which includes a support and a vitrification solution absorber including an adhesive layer and a vitrification solution absorbing layer in the given order on the support, and which has a structure including a portion with no adhesive layer disposed between the support and a portion of the vitrification solution absorbing layer configured to hold a cell or tissue. For example, the device may have a gripper together with the vitrification solution absorber. The gripper provides smooth handling of the device in the cryopreservation and thawing procedures, and thus is preferred.

Figure 1:
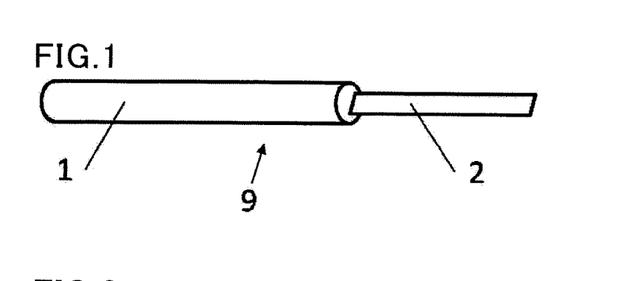
FIG. 1 is an overall view illustrating one example of the device for vitrification cryopreservation of a cell or tissue of the present invention.
Figure 2:
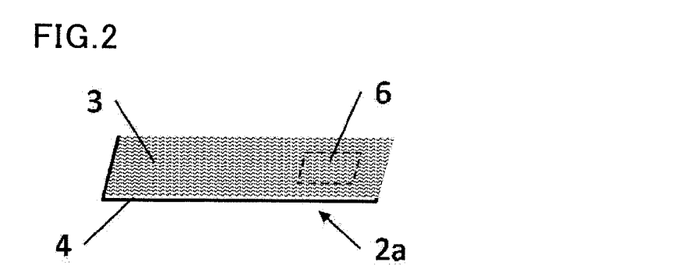
FIG. 2 is an enlarged view of a vitrification solution absorber of FIG. 1 excluding a gripper.

FIG. 1 is an overall view illustrating one example of the device for vitrification cryopreservation of a cell or tissue of the present invention. In FIG. 1, a device 9 for vitrification cryopreservation includes a gripper 1 and a vitrification solution absorber 2. FIG. 2 is an enlarged view of a vitrification solution absorber of FIG. 1 excluding a gripper. In FIG. 2, a vitrification solution absorber 2a has a structure in which a vitrification solution absorbing layer 3 is disposed on a support 4 (an adhesive layer is not illustrated), and has a portion 6 with no adhesive layer disposed between the vitrification solution absorbing layer and the support, which is surrounded by dotted lines. The portion 6 with no adhesive layer disposed between the vitrification solution absorbing layer and the support is to serve as a portion configured to hold a cell or tissue.

The gripper 1 illustrated in FIG. 1 is preferably made from a liquid nitrogen-resistant material. Preferred examples of such a material include various metals such as aluminum, iron, copper, and stainless steel alloy, ABS resin, polypropylene resin, polyethylene resin, fluorine resin, various engineering plastics, and glass. In FIG. 1, the gripper 1 has a cylindrical shape. Still, the gripper may have any shape. As will be mentioned later, in some cases, a cap may be placed on the vitrification solution absorber holding a cell or tissue before freezing so as to avoid direct contact between the cell or tissue and liquid nitrogen. In this case, the gripper 1 may be tapered such that the diameter of the cylinder continually decreases from the side with no vitrification solution absorber 2 to the side with the vitrification solution absorber 2, thereby improving the handleability when placing a cap. The vitrification solution absorber 2 is preferably in the form of a strip or sheet for easy handling.

The following will describe a method for connecting the gripper 1 and the vitrification solution absorber 2 as illustrated in FIG. 1. If the gripper 1 is made from resin, the vitrification solution absorber 2 may be connected to the gripper 1 by insert molding in the course of molding processing, for example. Alternatively, the vitrification solution absorber 2 may be connected to the gripper 1 using an adhesive by forming a structure-inserting part (not illustrated) in the gripper 1. Various adhesives may be used, and preferred are silicon or fluorine adhesives which are resistant to low temperatures.

Figure 3:
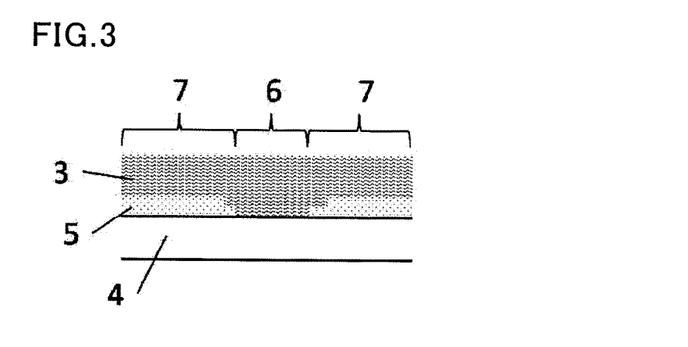
FIG. 3 is a schematic cross-sectional view of a portion 6 with no adhesive layer disposed between the vitrification solution absorbing layer and the support in the vitrification solution absorber illustrated in FIG. 2.

FIG. 3 is a schematic cross-sectional view of a portion 6 with no adhesive layer disposed between the vitrification solution absorbing layer and the support in the vitrification solution absorber illustrated in FIG. 2. In FIG. 3, the vitrification solution absorbing layer 3 has the portion 6 with no adhesive layer disposed between the vitrification solution absorbing layer and the support and a portion 7 with an adhesive layer disposed between the vitrification solution absorbing layer and the support. In FIG. 3, on the support 4, there is no space in the portion 6 with no adhesive layer disposed between the vitrification solution absorbing layer and the support, and the support 4 and the vitrification solution absorbing layer 3 are in direct contact with each other. As mentioned above, during formation of the portion 6 with no adhesive layer disposed between the vitrification solution absorbing layer and the support, a portion not coated with the adhesive composition is formed on the support 4, and then any of various sheets such as fibrous sheets, porous resin sheets, porous metal sheets, and porous metal oxide sheets is stacked before drying of the adhesive composition. In this procedure, if the adhesive composition has sufficient fluidity, i.e., before drying of the adhesive composition progresses, the above sheet quickly absorbs the adhesive composition. This enables formation of a vitrification solution absorber as illustrated in FIG. 3, i.e., having no space in the portion 6 with no adhesive layer disposed between the vitrification solution absorbing layer and the support and a structure in which the support 4 and the vitrification solution absorbing layer 3 are in direct contact with each other. In other words, the adhesive composition before the progress of drying is taken into the vitrification solution absorbing layer 3 to form the adhesive layer 5. Thus, no space is formed between the support 4 and the vitrification solution absorbing layer 3 in the portion 6 with no adhesive layer disposed between the vitrification solution absorbing layer and the support.

In contrast, if the adhesive composition is dried and the adhesive composition has insufficient fluidity, any of various sheets such as fibrous sheets, porous resin sheets, porous metal sheets, and porous metal oxide sheets has difficulty in quickly absorbing the adhesive composition. Thus, a space may be formed between the support 4 and the vitrification solution absorbing layer 3 in the portion 6 with no adhesive layer disposed between the vitrification solution absorbing layer and the support.

In the portion 6 with no adhesive layer disposed between the vitrification solution absorbing layer and the support, either of the vitrification solution absorber in which the support 4 and the vitrification solution absorbing layer 3 are in direct contact with each other or the vitrification solution absorber in which a space is formed between the support 4 and the vitrification solution absorbing layer 3 can sufficiently absorb an excess vitrification solution deposited around the cell or tissue. In contrast, if a space is formed between the support 4 and the vitrification solution absorbing layer 3, it may impair the visibility of a cell or tissue (visibility under microscopic observation) in thawing of the cryopreserved cell or tissue. The thawing procedure is performed such that isolation of the cell or tissue from the vitrification solution absorber and collection of the cell or tissue in a thawing solution separately prepared are observed under a transmission optical microscope. In this procedure, if there is a space between the support 4 and the vitrification solution absorbing layer 3, it may cause fluctuation of the vitrification solution absorbing layer 3 in the thawing solution and a failure in keeping the focus constant, impairing the visibility. Thus, the support 4 and the vitrification solution absorbing layer 3 are preferably in contact with each other in the portion 6 with no adhesive layer disposed between the vitrification solution absorbing layer and the support.

Figure 4:
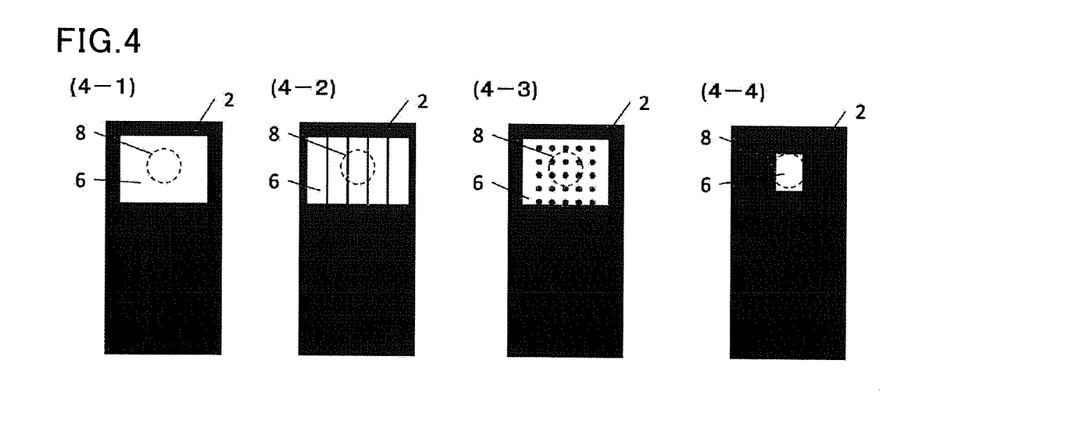
FIG. 4 is a schematic view of the structure of the vitrification solution absorber including a portion configured to hold a cell or tissue.

FIG. 4 is a schematic view of the structure of the vitrification solution absorber including a portion configured to hold a cell or tissue. In FIG. 4, FIG. (4-1) illustrates one example of the vitrification solution absorber 2 in which the whole portion 8 configured to hold a cell or tissue is the portion 6 with no adhesive layer disposed between the vitrification solution absorbing layer and the support. FIG. (4-2) illustrates one example of the vitrification solution absorber 2 in which part of the portion 8 configured to hold a cell or tissue has a striped adhesive layer. FIG. (4-3) illustrates one example of the vitrification solution absorber 2 in which part of the portion 8 configured to hold a cell or tissue has a dotted adhesive layer. The examples of FIGS. (4-1) to (4-3) are also examples of the vitrification solution absorber 2 in which the portion 8 configured to hold a cell or tissue is entirely included in the portion 6 with no adhesive layer disposed between the vitrification solution absorbing layer and the support. In contrast, FIG. (4-4) illustrates one example of the vitrification solution absorber 2 in which part of the portion 8 configured to hold a cell or tissue is outside the portion 6 with no adhesive layer disposed between the vitrification solution absorbing layer and the support.

In long-term cryopreservation of a cell or tissue using the device for vitrification cryopreservation of a cell or tissue of the present invention, the cell or tissue may be covered with a cap or the device for vitrification cryopreservation may be sealed in a container in any form to be isolated from the outside environment. Liquid nitrogen is usually non-sterile, and hence a cell or tissue frozen by direct contact with liquid nitrogen is not always guaranteed to be in a sterilized condition even if the device for vitrification cryopreservation is sterilized. Thus, the vitrification solution absorber holding a cell or tissue is occasionally covered with a cap or the device for vitrification cryopreservation is sealed in a container before the freezing procedure so as not to cause direct contact of a cell or tissue with liquid nitrogen. As mentioned above, a freezing method without direct contact with liquid nitrogen is the mainstream in developed countries such as EU. For this reason, the cap and the container are preferably made from any of liquid nitrogen-resistant material such as various metals, various resins, glass, and ceramics. They may have any shape as long as they are not brought into contact with the vitrification solution absorber and can shield a cell or tissue from the outside environment. The cap may have any shape, such as a half-spindle-shaped or dome-shaped cap like a cap for pencils, or a cylindrical straw cap. The container may be any one capable of including or storing the device for vitrification cryopreservation to seal it without contact with a cell or tissue on the vitrification solution absorber, and may have any shape.

In the present invention, the device for vitrification cryopreservation may be used in combination with such a cap or container capable of shielding a cell or tissue on the vitrification solution absorber from the outside environment as long as the effects of the present invention are not impaired. The device for vitrification cryopreservation used in combination with such a cap or container is also included in the present invention.

Figure 5:
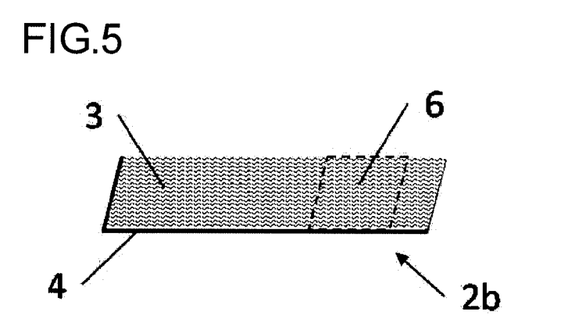
FIG. 5 is a schematic view illustrating another example of the vitrification solution absorber in the present invention.
Figure 6:
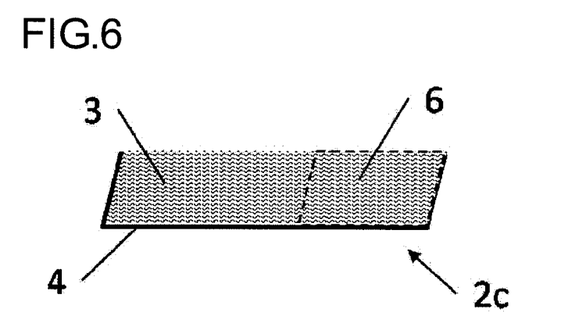
FIG. 6 is a schematic view illustrating another example of the vitrification solution absorber in the present invention.
Figure 7:
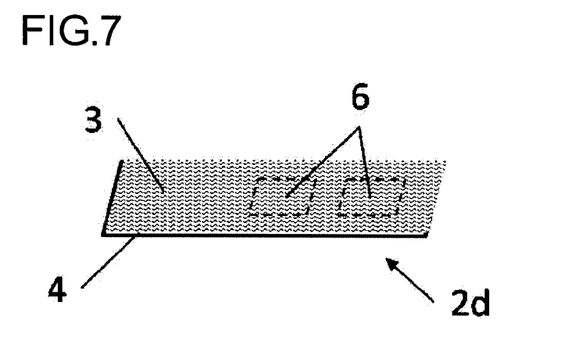
FIG. 7 is a schematic view illustrating another example of the vitrification solution absorber in the present invention.

FIG. 5 to FIG. 7 are each a schematic view illustrating another example of the vitrification solution absorber in the present invention. The vitrification solution absorber 2 of the device 9 for vitrification cryopreservation illustrated in FIG. 1 may be replaced by any of the vitrification solution absorbers 2b to 2d as illustrated in FIGS. 5 to 7.

In FIG. 5, the vitrification solution absorber 2b includes the vitrification solution absorbing layer 3 on the support 4, and the vitrification solution absorbing layer 3 is fixed on the support 4 by adhesive layers (not illustrated) present on the right and left sides (two opposite sides) of the portion 6 with no adhesive layer disposed between the vitrification solution absorbing layer and the support in the figure. In FIG. 6, the vitrification solution absorber 2c includes the vitrification solution absorbing layer 3 on the support 4, and the vitrification solution absorbing layer 3 is fixed on the support 4 by an adhesive layer (not illustrated) present on the left side of the portion 6 with no adhesive layer disposed between the vitrification solution absorbing layer and the support in the figure. In FIG. 7, the vitrification solution absorber 2d includes the vitrification solution absorbing layer 3 on the support 4. The vitrification solution absorbing layer 3 includes a plurality of the portions 6 with no adhesive layer disposed between the vitrification solution absorbing layer and the support, and is fixed on the support 4 by an adhesive layer (not illustrated) present on positions other than the portions 6 (on every surrounding side of the portions 6) with no adhesive layer disposed between the vitrification solution absorbing layer and the support. The vitrification solution absorbing layer 3 in the present invention is preferably fixed on the support 4 by an adhesive layer present on at least two surrounding sides (preferably two opposite sides) of the portion 6 with no adhesive layer disposed between the vitrification solution absorbing layer and the support. This reduces the fluctuation of the vitrification solution absorbing layer 3 in the thawing solution, leading to a device for vitrification cryopreservation providing excellent visibility of a cell or tissue in thawing a cryopreserved cell or tissue.

The vitrification solution absorber 2d illustrated in FIG. 7 is also one example of the structure of the vitrification solution absorber including a plurality of the portions 6 with no adhesive layer disposed between the vitrification solution absorbing layer and the support in the continuous vitrification solution absorbing layer 3.

The device for vitrification cryopreservation of the present invention may be preferably used in the Cryotop method, for example. The conventional Cryotop method is usually used for storage of a single cell or a small number of cells (e.g., less than 10 cells). In contrast, the device for vitrification cryopreservation of the present invention can also be suitably used for storage of a larger number of cells (e.g., storage of 10 to 1000000 cells). It can also be suitably used for storage of sheet-like cells (what is called cell sheets) formed from multiple cells. The use of the device for vitrification cryopreservation of the present invention reduces the damage to a cell or tissue from the vitrification solution outside the cell in the freezing and thawing procedures, thereby leading to good viability of the cell or tissue after the cryopreservation.

A method for cell or tissue cryopreservation using the device for vitrification cryopreservation of the present invention at least includes: immersing a cell or tissue in a vitrification solution; depositing dropwise the cell or tissue immersed in the vitrification solution on a vitrification solution absorber together with the vitrification solution, and thereby allowing a vitrification solution absorbing layer to absorb the vitrification solution surrounding the cell or tissue and to hold the cell or tissue; and immersing the device for vitrification cryopreservation holding the cell or tissue into, for example, liquid nitrogen to quickly freeze the cell or tissue. Before the immersion of the cell or tissue in the vitrification solution, the method may include an equilibrating step of immersing the cell or tissue into a pre-treatment solution containing a lower concentration of a cryoprotectant than in the vitrification solution. Alternatively, before the quick freezing of the cell or tissue, the method may include covering the vitrification solution absorber with a cap for shielding the cell or tissue on the vitrification solution absorbing layer from the outside environment or sealing the device for vitrification cryopreservation in the aforementioned container.

The quick freezing herein does not mean what is called slow freezing at a relatively low cooling rate (e.g., 0.3° C. to 0.5° C./min), but means freezing at a high cooling rate using a very low-temperature refrigerant (e.g., liquid nitrogen) while minimizing formation of ice crystals. The cooling rate in quick freezing is preferably 200° C./rain or higher from 0° C. to −150° C. measured using sheathed thermocouples (Chino Corp., tip outer diameter: 0.3 mm), for example. The vitrification solution may be one usually used for freezing cells, such as eggs and embryos. For example, the aforementioned aqueous solution containing a cryoprotectant, such as glycerol, ethylene glycol, or dimethyl sulfoxide (DMSO), may be used. The concentration of the cryoprotectant in the vitrification solution is usually 20 to 60%, as disclosed in Patent Literature 2.

In the thawing of the cryopreserved cell or tissue, preferably, the vitrification solution absorber holding the cryopreserved cell or tissue is immersed in a thawing solution so that the cell is thawed and simultaneously the vitrification solution is diluted. Such a procedure can minimize re-formation of ice crystals and ease the toxicity of the vitrification solution.

Examples of the cell that can be cryopreserved using the device for vitrification cryopreservation of the present invention include reproductive cells such as eggs, embryos, and sperms from mammals (for example, human, bovine, swine, horse, rabbit, rat, and mouse); and pluripotent stem cells such as induced pluripotent stem cells (iPS cells) and embryonic stem cells (ES cells). Also included are culture cells such as primary culture cells, subculture cells, and cell lines. In one or more embodiments, examples of the cell include adhesive cells such as fibroblasts, cancer-derived cells (e.g., pancreatic cancer cells and hepatoma cells), epithelial cells, vascular endothelial cells, lymphatic endothelial cells, neuronal cells, chondrocytes, tissue stem cells, and immune cells. Examples of the tissue that can be cryopreserved include tissues formed of homologous cells and tissues formed of heterologous cells, such as tissues of ovary, skin, corneal epithelium, periodontal ligament, and myocardium. The present invention is particularly suitable for vitrification cryopreservation of tissues having a sheet-like structure (e.g., cell sheets and skin tissues). The device for vitrification cryopreservation of the present invention can be suitably used for vitrification cryopreservation of not only native tissues harvested from living bodies but also artificial tissues, such as cultured skins formed by in vitro expansion of cells, what is called cell sheets formed in vitro, and a three-dimensional tissue model described in JP 2012-205516 A. The device for vitrification cryopreservation of the present invention is suitably used as a device for vitrification cryopreservation of the aforementioned cells or tissues.

EXAMPLES

The present invention will be more specifically described hereinbelow referring to, but not limited to, the following non-limiting examples.

Example 1

First, 40 parts by mass of stretch-crystallized polyethylene terephthalate staple fibers having a fineness of 0.06 dtex (fiber diameter: about 2 μm) and a cutlength of 3 mm, 20 parts by mass of stretch-crystallized polyethylene terephthalate staple fibers having a fineness of 0.1 dtex (fiber diameter: about 3 μm) and a cutlength of 3 mm, and 40 parts by mass of non-stretched polyethylene terephthalate staple fibers having a fineness of 0.2 dtex (fiber diameter: about 4 μm) and a cutlength of 3 mm were formed into a sheet by a wet papermaking process. The sheet was then passed through heating calender rolls at a surface temperature of 200° C. so that the staple fibers were fused and the thickness of the sheet was adjusted. Thereby, a nonwoven fabric (vitrification solution absorbing layer) having an average fiber diameter of 3.0 μm, a grammage of 25 g/m$^2$, and a density of 0.5 g/cm$^3$ was obtained.

A 5 mass % aqueous solution of PVA 235 (Kuraray Co., Ltd.) serving as an adhesive layer was applied to a transparent PET film support (total light transmittance: 91%, haze value: 5.5%), which had been subjected to easy adhesion treatment, such that the dry solid content of the adhesive layer was 30 g/m$^2$. The above vitrification solution absorbing layer was immediately stacked on the adhesive layer before drying of the adhesive layer applied, and then the adhesive layer was sufficiently dried at 70° C. Before the application of the adhesive layer, part of the transparent PET film support was masked to form a portion not coated with the adhesive layer. Thereby, a vitrification solution absorber as illustrated in FIG. 5 was produced. This vitrification solution absorber was connected to a gripper made from ABS resin. Thereby, a device for vitrification cryopreservation of Example 1 as illustrated in FIG. 1 was produced. The vitrification solution absorber of the device for vitrification cryopreservation of Example 1 had a size of 40 mm$^2$ (2 mm×20 mm), and the portion with no adhesive layer disposed between the vitrification solution absorbing layer and the support had a size of 10 mm$^2$ (2 mm×5 mm). The device for vitrification cryopreservation of Example 1 is one embodiment expected to be used particularly in a method including dropwise deposition of multiple cells or tissues with a relatively large amount of a vitrification solution and cryopreservation and thawing procedures.

Example 2

A device for vitrification cryopreservation of Example 2 was produced in the same manner as in the production of the device for vitrification cryopreservation of Example 1 except that Purmelt QR 170-7141P (Henkel Japan Ltd.), which is a hot melt urethane resin, was applied as an adhesive layer to a transparent PET film support, which had been subjected to easy adhesion treatment, such that the dry solid content of the adhesive layer was 30 g/m².

Example 3

A device for vitrification cryopreservation of Example 3 was produced in the same manner as in the production of the device for vitrification cryopreservation of Example 2 except that filter paper No. 5C (Advantec Toyo Kaisha, Ltd., grammage: 120 g/m², density: 0.57 g/cm³, thickness: 210 μm) was stacked as a vitrification solution absorbing layer on the adhesive layer while the adhesive layer applied was heated using a dryer.

Comparative Example 1

A device for vitrification cryopreservation of Comparative Example 1 was produced in the same manner as in the production of the device for vitrification cryopreservation of Example 2 except that the adhesive layer was applied to the entire surface of the transparent PET film support without forming a portion not coated with the adhesive layer, and a vitrification solution absorbing layer was stacked thereon before the adhesive layer was dried.

Comparative Example 2

A device for vitrification cryopreservation of Comparative Example 2 was produced in the same manner as in the production of the device for vitrification cryopreservation of Example 3 except that the adhesive layer was applied to the entire surface of the transparent PET film support without forming a portion not coated with the adhesive layer, and a vitrification solution absorbing layer was stacked thereon before the adhesive layer was dried.

<Evaluation of Vitrification Solution Absorbency>

First, 1 μL of a vitrification solution containing multiple glass beads (diameter: 100 μm) as cell mimics were deposited dropwise on the vitrification solution absorbing layer in the portion (2 mm×5 mm) with no adhesive layer disposed between the vitrification solution absorbing layer and the support of each of the devices for vitrification cryopreservation of Examples 1 to 3. Similarly, 1 μL of a vitrification solution containing multiple glass beads (diameter: 100 μm) as cell mimics was deposited dropwise on the vitrification solution absorber layer of each of the devices for vitrification cryopreservation of Comparative Examples 1 and 2. The vitrification solution used contained a modified TCM199 medium (Sigma-Aldrich) plus 20 vol % serum, 15 vol % DMSO, 15 vol % ethylene glycol, and 0.2 vol % sucrose. After the dropwise deposition, absorption of the vitrification solution surrounding the cell mimics deposited on the vitrification solution absorbing layer was observed under a reflected upright optical microscope (VC4500-S1, Omron Corp.), and the vitrification solution absorbency was evaluated by the following criteria. Table 1 shows the results.

Good: An excess vitrification solution surrounding the cell mimics completely or almost disappeared within 10 seconds from the dropwise deposition of the vitrification solution.

Poor: An excess vitrification solution surrounding the cell mimics remained even after 10 seconds from the dropwise deposition of the vitrification solution.

TABLE 1

|  | Evaluation of absorbency |
| --- | --- |
| Example 1 | Good |
| Example 2 | Good |
| Example 3 | Good |
| Comparative Example 1 | Poor |
| Comparative Example 2 | Poor |

Example 4

A device for vitrification cryopreservation of Example 4 was produced in the same manner as in the production of the device for vitrification cryopreservation of Example 2 except that Bemliese® SE14G (Asahi Kasei Fibers Corp., grammage: 14 g/m², density: 0.19 g/cm³, thickness: 70 μm), which is a nonwoven fabric made from cupro fiber, was stacked as a vitrification solution absorbing layer on the adhesive layer while the adhesive layer applied was heated using a dryer.

Example 5

A device for vitrification cryopreservation of Example 5 was produced in the same manner as in the production of the device for vitrification cryopreservation of Example 2 except that Elleair® Prowipe Soft Microwiper S220 (Daio Paper Corp., grammage: 22 g/m², density: 0.21 g/cm³), which is paper, was stacked as a vitrification solution absorbing layer on the adhesive layer while the adhesive layer applied was heater using a dryer.

Example 6

A device for vitrification cryopreservation of Example 6 was produced in the same manner as in the production of the device for vitrification cryopreservation of Example 2 except that Sunfine AQ800 (Asahi Kasei Corp., micropore size: 35 μm, porosity: 43%, thickness: 500 μm), which is a porous resin sheet made from polyethylene resin, was stacked as a vitrification solution absorbing layer on the adhesive layer while the adhesive layer applied was heated using a dryer.

Example 7

A device for vitrification cryopreservation of Example 7 was produced in the same manner as in the production of the device for vitrification cryopreservation of Example 2 except that porous silica glass (Covalent Materials Corp., micropore size: 3.5 μm, porosity: 33%, thickness: 2 mm), which is a porous metal oxide sheet, was stacked as a vitrification solution absorbing layer on the adhesive layer while the adhesive layer applied was heated using a dryer.

Example 8

A device for vitrification cryopreservation of Example 8 was produced in the same manner as in the production of the device for vitrification cryopreservation of Example 2 except that hydrophilized porous polytetrafluoroethylene (Merck Millipore Corp., micropore size: 10 μm, porosity: 80%, thickness: 85 μm), which is a porous resin sheet made from polytetrafluoroethylene resin, was stacked as a vitrification solution absorbing layer on the adhesive layer while the adhesive layer applied was heated using a dryer.

Example 9

A device for vitrification cryopreservation of Example 9 was produced in the same manner as in the production of the device for vitrification cryopreservation of Example 1 except that hydrophilized porous polytetrafluoroethylene (Merck Millipore Corp., micropore size: 10 µm, porosity: 80%, thickness: 85 µm), which is a porous resin sheet made from polytetrafluoroethylene resin, was stacked as a vitrification solution absorbing layer on the adhesive layer while the adhesive layer applied was heated using a dryer.

Example 10

A device for vitrification cryopreservation of Example 10 was produced in the same manner as in the production of the device for vitrification cryopreservation of Example 2 except that porous polyvinylidene difluoride (Merck Millipore Corp., micropore size: 0.5 µm, porosity: 70%, thickness: 125 µm), which is a porous resin sheet made from polyvinylidene difluoride resin, was stacked as a vitrification solution absorbing layer on the adhesive layer while the adhesive layer applied was heated using a dryer.

<Evaluation of Vitrification Solution Absorbency>

The vitrification solution absorbency of each of the devices for vitrification cryopreservation obtained in Examples 4 to 10 as mentioned above were evaluated in the same manner as in the above cases of the devices for vitrification cryopreservation of Examples 1 to 3 and Comparative Examples 1 and 2. Table 2 shows the results.

<Evaluation of Visibility of Cell Mimics>

In the same manner as in the aforementioned "Evaluation of vitrification solution absorbency", cell mimics were deposited dropwise with the vitrification solution on the vitrification solution absorbing layer in the portion (2 mm×5 mm) with no adhesive layer disposed between the vitrification solution absorbing layer and the support of each of the devices for vitrification cryopreservation of Examples 4 to 10. Whether or not the cell mimics deposited on the vitrification solution absorber were observable under a transmission optical microscope (SZH-121, Olympus Corp.) was evaluated by the following criteria. Table 2 shows the results.

Excellent: The shapes of the cell mimics were clearly observed.

Good: The shapes of the cell mimics were observed.

Acceptable: The presence of the cell mimics were confirmed, but the shapes thereof were not observed.

Poor: The presence of the cell mimics were difficult to confirm.

TABLE 2

|  | Evaluation of absorbency | Evaluation of visibility |
| --- | --- | --- |
| Example 4 | Good | Acceptable |
| Example 5 | Good | Acceptable |
| Example 6 | Good | Acceptable |
| Example 7 | Good | Acceptable |
| Example 8 | Good | Excellent |
| Example 9 | Good | Excellent |
| Example 10 | Good | Excellent |

Table 2 shows that the device for vitrification cryopreservation of the present invention provides excellent performance of absorbing a vitrification solution as well as excellent visibility.

INDUSTRIAL APPLICABILITY

The present invention can be applied to cryopreservation of cells or tissues such as cells or tissues for embryo transfer and artificial insemination of domestic animals (e.g., cattle) and other animals, and for human artificial insemination; iPS cells; ES cells; commonly used culture cells; cells or tissues harvested from living bodies for the purpose of examination or implantation; and cells or tissues cultured in vitro.

REFERENCE SIGNS LIST

1: gripper
2, 2a to 2d: vitrification solution absorber
3: vitrification solution absorbing layer
4: support
5: adhesive layer
6: portion with no adhesive layer disposed between vitrification solution absorbing layer and support
7: portion with an adhesive layer disposed between vitrification solution absorbing layer and support
8: portion configured to hold a cell or tissue
9: device for vitrification cryopreservation

The invention claimed is:

1. A device for vitrification cryopreservation of a cell or tissue, comprising:
 a support; and
 a vitrification solution absorber including at least an adhesive layer and a vitrification solution absorbing layer in the given order on the support,
 the device including a portion with no adhesive layer disposed between the support and a portion of the vitrification solution absorbing layer configured to hold a cell or tissue.

2. The device for vitrification cryopreservation of a cell or tissue according to claim 1,
 wherein the support is a light-transmitting support, and the vitrification solution absorbing layer is at least one selected from paper or nonwoven fabric having a density of 0.12 to 0.3 g/cm$^3$ and a grammage of 10 to 100 g/m$^2$, porous resin sheets, and porous metal oxide sheets.

* * * * *